United States Patent
Vallittu

(10) Patent No.: US 11,013,603 B2
(45) Date of Patent: May 25, 2021

(54) ORTHOPEDIC IMPLANT

(71) Applicant: Skulle Implants Oy, Turku (FI)

(72) Inventor: Pekka Vallittu, Kuusisto (FI)

(73) Assignee: Skulle Implants Oy, Turku (FI)

( * ) Notice: Subject to any disclaimer, the term of this patent is extended or adjusted under 35 U.S.C. 154(b) by 0 days.

(21) Appl. No.: 15/741,822

(22) PCT Filed: Jul. 1, 2016

(86) PCT No.: PCT/EP2016/065545
§ 371 (c)(1),
(2) Date: Jan. 4, 2018

(87) PCT Pub. No.: WO2017/005637
PCT Pub. Date: Jan. 12, 2017

(65) Prior Publication Data
US 2018/0200064 A1   Jul. 19, 2018

(30) Foreign Application Priority Data
Jul. 8, 2015   (EP) ..................... 15175784

(51) Int. Cl.
*A61L 27/10* (2006.01)
*A61F 2/30* (2006.01)
(Continued)

(52) U.S. Cl.
CPC ........ *A61F 2/30965* (2013.01); *A61F 2/2875* (2013.01); *A61L 27/10* (2013.01);
(Continued)

(58) Field of Classification Search
CPC .......... A61F 2/2875; A61F 2002/30062; A61F 2002/3092; A61F 2002/2825;
(Continued)

(56) References Cited

U.S. PATENT DOCUMENTS

| 4,186,448 A | 2/1980 | Brekke |
| 8,864,825 B2 | 10/2014 | Vallittu |

(Continued)

FOREIGN PATENT DOCUMENTS

| WO | 8803417 | 5/1988 |
| WO | 0015152 | 3/2000 |

(Continued)

*Primary Examiner* — Christopher D. Prone
(74) *Attorney, Agent, or Firm* — James C. Lydon

(57) ABSTRACT

An implant having a surface layer consisting of fibres and a matrix, having a first surface opposite to a second surface, and having a thickness that is at most 5% of the largest dimension of the surface layer; a porous biodegradable part having a first surface and opposite to a second surface, where its first surface is attached to the surface layer's second surface and having a thickness of 1-8 mm; and a collagen membrane layer having a first surface opposite to a second surface, where its first surface is attached to the porous part's second surface without covering the porous part's edges; and where the porous part comprises material selected from the group consisting of bioactive glass, bioactive ceramic, hydroxyapatite, tricalciumphosphate and mixtures thereof.

13 Claims, 3 Drawing Sheets

(51) Int. Cl.
  *A61F 2/28* (2006.01)
  *A61L 27/12* (2006.01)
  *A61L 27/56* (2006.01)
  *A61L 27/58* (2006.01)
  *A61L 27/32* (2006.01)
  *A61L 27/34* (2006.01)
  *A61L 27/30* (2006.01)
  *A61L 27/26* (2006.01)
  *A61L 27/54* (2006.01)

(52) U.S. Cl.
  CPC ............... *A61L 27/12* (2013.01); *A61L 27/26* (2013.01); *A61L 27/303* (2013.01); *A61L 27/32* (2013.01); *A61L 27/34* (2013.01); *A61L 27/54* (2013.01); *A61L 27/56* (2013.01); *A61L 27/58* (2013.01); *A61F 2002/2825* (2013.01); *A61F 2002/30011* (2013.01); *A61F 2002/30032* (2013.01); *A61F 2002/30062* (2013.01); *A61F 2002/3092* (2013.01); *A61F 2002/30578* (2013.01); *A61F 2002/30971* (2013.01); *A61F 2310/00179* (2013.01); *A61F 2310/00329* (2013.01); *A61F 2310/00371* (2013.01); *A61F 2310/00982* (2013.01); *A61L 2430/02* (2013.01)

(58) Field of Classification Search
  CPC .. A61F 2002/3071; A61L 27/10; A61L 27/12; A61L 27/54
  See application file for complete search history.

(56) References Cited

U.S. PATENT DOCUMENTS

| | | | |
|---|---|---|---|
| 9,084,844 B2 | 7/2015 | Vallittu | |
| 9,144,630 B2 | 9/2015 | Vallittu et al. | |
| 2005/0113930 A1* | 5/2005 | Ganz | A61C 8/0006 623/17.17 |
| 2007/0041952 A1 | 2/2007 | Guilak et al. | |
| 2007/0083268 A1* | 4/2007 | Teoh | A61L 31/148 623/17.19 |
| 2016/0243283 A1 | 8/2016 | Karhi et al. | |

FOREIGN PATENT DOCUMENTS

| | | |
|---|---|---|
| WO | 2010086508 | 8/2010 |
| WO | 2013178637 | 5/2013 |

\* cited by examiner

ORTHOPEDIC IMPLANT

FIELD OF THE INVENTION

The invention relates to an implant, which is especially useful in craniomaxiofacial orthopedic surgery.

BACKGROUND

The use of reinforced composites made of particulate fillers or reinforcing fibres is already known. The state-of-the-art fibre reinforced composites yield high strength properties and by selecting the multiphase resin matrix for the composite, the handling characteristics of the composite can be considerably improved.

On the other hand, a lot of development has occurred with bioactive materials, namely bioactive ceramics and glass and sol-gel processed silica. These materials can be used to achieve attachment of e.g. bone to a biomaterial surface after the material has been put in contact with tissue. An additional advantage of bioactive glass is its antimicrobial effect on the microbes. However, bioactive ceramics and glasses are rather brittle and cannot thus easily be used as such in implants.

For example, document WO 88/03417 presents a biocomposite material for bone surgical applications comprising at least one bioceramic piece and at least one material component which has been manufactured of at least one polymer or corresponding material. The material component has at least one common boundary surface with the bioceramic component and the material component comprises at least reinforcement elements which have been manufactured of essentially resorbable material like polymer, copolymer, polymer mixture and/or ceramic material. The material component can include binding material which is manufactured essentially of resorbable polymer, copolymer or polymer mixture. The material component contains open porosity, at least in tissue conditions.

From a surgical perspective, individual replacement of bone, cartilage and soft tissues are insufficient in tumour, traumatologic and tissue reconstruction surgery despite the increasing advances in biomaterials research and their clinical application methods and tissue engineering. The need and indications for development of new kinds of materials result from disadvantages of the use of allografts. Metals are not bioactive or osteoconductive, and their use results in stress shielding phenomena and bone atrophy of the adjacent bone. Metal implants cause also severe problems in magnetic resonance imaging (MRI) when diagnosing diseases of patients and also due to heating of the implant during imaging. There thus still exists a need for alternative implants for medical uses.

OBJECTS AND SUMMARY OF THE INVENTION

An object of the present invention is to provide a biologically compatible material that does not have the above-listed drawbacks, or at least those disadvantages are minimised. Specifically, an object of the present invention is to provide an implant useful for medical, dental and surgical uses, such as for bone grafting in repair of bone defects and fixation of fractured pieces of bone.

A typical implant according to this description consists of
- a surface layer consisting of fibres and a matrix, having a first surface and a second surface opposite each other, and having a thickness that is at most 5% of the largest dimension of said surface layer,
- a porous biodegradable part having a first surface and a second surface opposite each other, wherein its first surface is attached to the second surface of the surface layer and having a thickness of 1-8 mm, and
- a membrane layer made of collagen having a first surface and a second surface opposite each other, wherein its first surface is attached to the second surface of the porous part without covering the edges of the porous part, wherein the porous part comprises material selected from the group consisting of bioactive glass, bioactive ceramic, hydroxyapatite, tricalciumphosphate and mixtures thereof.

DETAILED DESCRIPTION OF THE INVENTION

Figure 1:
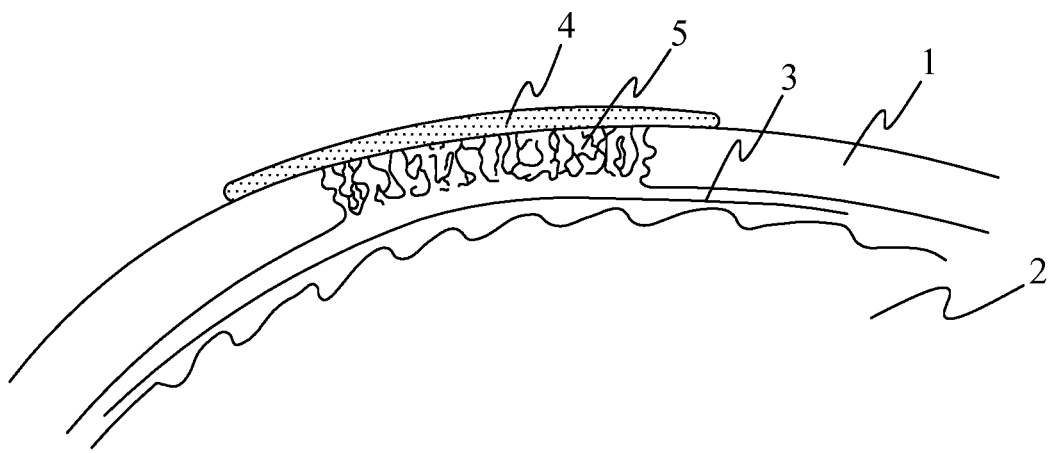
FIG. 1 schematically shows an implant according to a first embodiment.

A typical implant according to this description consists of
- a surface layer consisting of fibres and a matrix, having a first surface and a second surface opposite each other, and having a thickness that is at most 5% of the largest dimension of said surface layer,
- a porous biodegradable part having a first surface and a second surface opposite each other, wherein its first surface is attached to the second surface of the surface layer and having a thickness of 1-8 mm, and
- a membrane layer made of collagen having a first surface and a second surface opposite each other, wherein its first surface is attached to the second surface of the porous part without covering the edges of the porous part, wherein the porous part comprises material selected from the group consisting of bioactive glass, bioactive ceramic, hydroxyapatite, tricalciumphosphate and mixtures thereof.

The implant according to this description thus takes advantage of the capillary effect, as fluids can penetrate inside of the biodegradable, porous part of the implant. The porous part of the implant thus enhances the growth of new bone, cartilage etc. and the non-biodegradable surface layer provides the mechanical strength and anatomical form. A further advantage is that it allows to manufacture implant material that is very much similar to real bone, i.e. to avoid using allografts. On the other hand, traditional metallic implants are less desired due to the increase of magnetic resonance imaging. The present invention thus provides for an implant that is both safe (no risk of contamination as with allografts) and that does interfere with currently used imaging systems (as metal does).

In this specification, by curing it is meant polymerisation and/or crosslinking. By matrix, it is understood the continuous phase of a composition and by uncured matrix it is meant a matrix that is in its deformable state but that can be cured, i.e. hardened, to an essentially non-deformable state. The uncured matrix may already comprise some long chains but it is essentially not yet polymerised and/or crosslinked.

In the present description, the polymerisation may be performed by any known way, such as autopolymerisation, light polymerisation, thermal polymerisation, ultrasound or microwave polymerisation. The curing of a resin leads to a composite material, wherein the cured resin forms the matrix.

The surface layer may be either porous or non-porous, wherein non-porous means a material that is essentially impermeable to fluids present in the site of implantation. In case the surface layer is porous, i.e. perforated (either due to its material or after a specific perforation step during its manufacture), its porosity is preferably smaller than the porosity of the biodegradable part. For example, its average pore size may be 0.8-500 micrometers.

The biodegradable part is a porous part, having a continuous porosity with an average pore size of 100-1000 micrometers. The porosity is such that extracellular fluids and cells can penetrate the porous part and allow ingrowth of bone, blood cells and other tissues. The porous part typically degrades in a time frame that varies from a few weeks (for example a biodegradable polymer) to a few years (for example hydroxyapatite), while at the same time it is replaced by new bone. An optimal pore size for endosseus applications is 100 to 500 micrometers when bone ingrowth is considered, but the porous part may optionally also contain larger holes. Furthermore, the inner surface of the porous part may be mostly covered with a membrane-like material made of collagen (for example Durepair Dura Regeneration Matrix™ by Medtronic) in order to reduce attachment of dura mater to the implant. This may be advantageous for some instances, for example for patients having an increased pressure in the brain, which would cause the dura to be in contact with the surface of the porous part. The membrane-like material does not entirely cover the surface of the porous part but leaves its edges exposed. This ensures that body fluids can penetrate the porous part. For example, 1-2 mm of each edge can be left uncovered by the membrane, when considered from the edge of the porous part.

The thickness of the surface layer can be for example 0.2-4.0 mm. For example, in cranial applications a thickness of 0.5-1.0 mm could be suitable for the surface layer and in load bearing implants, a thickness of 1.0-3.0 mm could be suitable for this layer. In general, the thickness of the surface layer can be from 0.2, 0.3, 0.5, 0.7, 1, 1.5, 1.7, 2, 2.5, 3 or 3.5 mm up to 0.3, 0.5, 0.7, 1, 1.5, 1.7, 2, 2.5, 3, 3.5 or 4.0 mm.

The thickness of the membrane made of collagen can be for example 0.05-0.80 mm. The thickness can be for example from 0.05, 0.1, 0.15, 0.2, 0.25, 0.3, 0.35, 0.4, 0.45, 0.5, 0.55, 0.6, 0.65, 0.7 or 0.75 mm, up to 0.1, 0.15, 0.2, 0.25, 0.3, 0.35, 0.4, 0.45, 0.5, 0.55, 0.6, 0.65, 0.7, 0.75 or 0.8 mm The porous part may be manufactured for example by sintering, laser sintering, moulding suitable material, electrospinning, 3D printing or by milling. The surface layer may be non-biodegradable, i.e. inert, or it may be biodegradable. The materials used are naturally selected based on the desired degradation rate. In case the surface layer is biodegradable, its degradation time is at least ten times longer than that of the porous part. This enables bone ingrowth and maturation to occur before the surface layer loses its mechanical strength. Slowly biodegradable outer surface laminate can be made for example of fibres of bioactive glass, calcium-sodium-metaphosphate, cellulose, hemp or starch and slowly degrading polylactide, polycaprolactone polymer or polysaccharide as matrix material.

One suitable example of bioactive glass is the glass S53P4, which is a resorbable bioactive glass with the composition of 53% $SiO_2$, 23% $Na_2O$, 20% CaO and 4% $P_2O_5$ (available for example from BonAlive Biomaterials Ltd in Turku, Finland).

In the case also the surface layer is biodegradable, the implant is preferably attached to the bone by slowly biodegradable screws. This allows the surgeon to avoid a second operation to remove the screws and is thus beneficial especially in operations performed on children.

The fibres of the surface layer which is non-biodegradable may be any suitable fibres known per se, for example selected from the group consisting of inert glass fibres, silica/quartz fibres, carbon/graphite fibres, inert ceramic fibres, aramid fibres, zylon fibres, polyethylene fibres, polytetrafluoroethylene fibres, such as Teflon® fibres, poly(p-phenylene-2,6-benzobisoxazole) fibres, poly(2,6-diimidazo (4,5-b4',5'-e)pyridinylene-1,4(2,5-dihydro)phenylene fibres, polyolefin fibres, fibres prepared from copolymers of olefins, polyester fibres, polyamide fibres and mixtures thereof. Poly(p-phenylene-2,6-benzobisoxazole) fibres and poly(2,6-diimidazo(4,5-b4',5'-e)pyridinylene-1,4(2,5-dihydro)phenylene fibres belong to a group called rigid-rod polymer fibres. It is obvious to a person skilled in the art that any other known fibres may be used in the present invention, provided that it is possible to obtain a suitable adhesion between said fibres and matrix, in order to achieve the desired mechanical properties and that the fibres are biocompatible.

According to one embodiment of the invention, the fibres are selected from the group consisting of inert glass fibres. According to another embodiment, the glass fibres are made of a glass composition of E-glass, S-glass, R-glass, C-glass or bioactive glasses.

According to yet another embodiment, the diameter of the fibres is 4-25 μm. The diameter of the fibres can be for example from 3, 5, 6, 10, 15, 20, 25, 30, 40, 45, 50, 60, 70 or 80 μm up to 5, 6, 10, 15, 20, 25, 30, 40, 45, 50, 60, 70, 80, 90 or 100 μm. Fibres in the nanometer scale, i.e. with a cross-sectional diameter varying between 200-1000 nm can also be used.

The fibres may be in the form of fibre fabrics or fibre mats, and they may be oriented in two directions, three directions, four directions or randomly thereof.

The matrix may be made of a resin consisting of monomers selected from the group consisting of methyl acrylate, ethyl acrylate, propyl acrylate, isopropyl acrylate, n-hexyl acrylate, styryl acrylate, allyl acrylate, methyl methacrylate, polymethyl methacrylate, ethyl methacrylate, propyl methacrylate, isopropyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diurethane dimethacrylate, acetoacetoxy ethyl methacrylate (AAEM), methacrylate functionalized dendrimers, other methacrylated hyperbranched oligomers, hydroxymethyl methacrylate, hydroxymethyl acrylate, hydroxyethyl methacrylate, hydroxyethyl acrylate, hydroxypropyl methacrylate, hydroxypropyl acrylate, tetrahydrofurfuryl methacrylate, tetrahydrofurfuryl acrylate, glycidyl methacrylate, glycidyl acrylate, triethylene glycol diacrylate, tetraethylene glycol dimethacrylate, tetraethylene glycol diacrylate, trimethylolethane trimethacrylate, trimethylolpropane trimethacrylate, pentaerythritol trimethacrylate, trimethylolethane triacrylate, trimethylolpropane triacrylate, pentaerythritol triacrylate, pentaerythritol tetramethacrylate, pentaerythritol tetra-acrylate, ethylene dimethacrylate, ethylene diacrylate, ethylene glycol dimethacrylate, diethylene glycol dimethacrylate, triethylene glycol dimethacrylate (TEGDMA), ethylene glycol diacrylate, diethyleneglycol diacrylate, butylene glycol dimethacrylate, butylene glycol diacrylate, neopentyl glycol dimethacrylate, hydroxyethyl methacrylate, urethan dimethacrylate, starburst methacrylated polyesters, hyperbranched methacrylated polyesters, neopentyl glycol diacrylate, 1,3-butanediol dimethacrylate, 1,3-butanediol diacrylate, 1,4-butanediol dimethacrylate, 1,4-butanediol diacrylate, 1,6-hexanediol dimethacrylate, 1,6-hexanediol diacrylate, di-2-methacryloxyethyl-hexametylene dicarbamate, di-2-methacryloxyethyl-trimethylhexametylene dicarbamate, di-2-methacryloxyethyl-dimethylbenzene dicarbamate, di-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl-4-cyclohexyl carbamate, 2,2-bis(4-(2-hydroxy-3-methacryloxy)phenyl)propane (BisGMA), 2,2'-bis(4-methacryloxyphenyl)propane, 2,2'-bis(4-acryloxyphenyl)propane, 2,2'-bis(4(2-hydroxy-3-acryloxyphenyl)propane, 2,2'-bis(4-methacryloxyethoxyphenyl)propane, 2,2'-bis(4-acryloxyethoxyphenyl)-propane, 2,2'-bis(4-methacryloxypropoxyphenyl)propane, 2,2'-bis(4-acryloxypropoxyphenyl)propane, 2,2'-bis(4-methacryloxydiethoxyphenyl)-propane, 2,2'-bis(4-acryloxydiethoxyphenyl)propane, 2,2'-bis[3(4-phenoxy)-2-hydroxypropane-1-methacrylate]propane, 2,2'-bis[3(4-phenoxy)-2-hydroxypropane-1-acrylate]propane, polyetheretherketone and mixtures thereof.

The matrix may naturally also consist of a mixture of a monomer(s) and a polymer(s).

According to one embodiment, the matrix material is an acrylate polymer. According to an embodiment, the matrix resin is selected from the group consisting of substituted and unsubstituted dimethacrylates and methacrylates. Some especially advantageous matrix materials (monomers) are methyl acrylate, methyl methacrylate, methacrylate functionalized dendrimers, glycidyl dimethacrylate (bis-GMA), triethylene glycol dimethacrylate (TEGDMA) and urethane dimethacrylate (UDMA). The materials may be used as blends and they may form interpenetrating polymer networks (IPNs). They may also be functionalised with bioactive molecules that allow for a drug-like contact effect. Combinations of monomers and polymers are also suitable to be used, including modifications of resin systems by antimicrobial side group containing iodine which offers additional benefit in increasing radio opacity of the resin system. When the matrix is biodegradable, any biocompatible and slowly biodegradable resin and polymer can be used.

The implant may further comprise modifier particles in the porous part. These modifier particles may for example be bioactive and for example improve the osteoconductivity of the implant. The particles may be in the form of particulate fillers or fibres. The weight fraction of these modifier particles in the implant can be for example 5-30 wt-%, such as from 5, 10, 15, 20 or 25 wt-% up to 10, 15, 20 or 30 wt-%.

According to one embodiment, the modifier particles are selected from the group consisting of bioactive ceramics, silica gel, titanium gel, silica xerogel, silica aerogel, natrium silica glass, titanium gels, bioactive glass ionomer, Ca/P-doped silica gel and mixtures thereof. Any combination of said materials may naturally also be used.

The porous part of the implant may yet further comprise additional particulate filler material, such as metal oxides, ceramics, polymers and mixtures thereof. Metal oxides may for example be used as radio or X-ray opaque materials or as colouring materials.

The porous part of the implant may also comprise therapeutically active agents or cells such as stem cells, proteins such as growth factors and/or signalling molecules. Several kinds of cells including hematopoietic bone marrow cells, fibroblasts, osteoblasts, regenerative cells, stem cells, like embryonic stem cells, mesenchymal stem cells or adipose stem cells can be seeded to the implant. The embryonic stem cells may or may not be of a human origin. Stem cells seeded to the implant can be cultured in bioreactors ex vivo, in other parts of the body before inserting the formed tissue into its final place, or directly at the place where regenerative and reconstructive treatment is needed.

The size and shape of the implant is selected according to the intended use. The diameter of the implant can be for example from 5 to 500 mm. According to an embodiment, the thickness of the implant is about 1.05-8.1 mm. The thickness of the implant depends typically on the thickness of the bone it intends to replace. The porous part typically forms a majority of the implant thickness, while the surface layer is significantly thinner.

The implant may also have different shapes as will be explained in more detail in connection with the drawing. The implant may thus has an essentially flat upper surface and an extension on the other surface. The surface layer of the implant typically had a shape that conforms to the anatomy of the bone it is intended to cover. The surface layer may thus be essentially flat, have a slightly concave form or be in an essentially U-shaped form (when used for long bones such as for legs or arms).

The surface layer is typically such that its thickness is dearly smaller than its other two dimensions (which other two dimensions define the largest surface area of the surface layer). The porous part has typically a shape of a cylinder or a rectangle, i.e. its thickness is larger with respect to its two other dimensions than the thickness of the surface layer. Furthermore, the surface area of the surface of the porous part that faces the surface layer is typically smaller than the surface area of the surface layer. Moreover, according to a preferred embodiment, the porous part is attached to the surface layer in such a position that the surface layer extends over each edge of the porous part. According to one embodiment, the porous part is attached essentially in the middle of the surface layer.

The surface layer thus typically extends over each edge of the porous part. This enables attachment of the implant to bone or other tissue, by any suitable means. For example, when used in brain surgery, the porous part has essentially the same shape and thickness as the piece of skull removed for surgery. The surface layer has a slightly larger surface area thus allowing the attachment of the implant to the skull. Indeed, the implant can be attached to the skull by screws at the edges of the surface layer. The surface layer may for example be provided with small holes for attachment. In this manner, the surface layer gives the porous layer extra strength during healing and bone ingrowth, which will greatly improve both the results of the surgery and the quality of life of the patient during healing.

A typical implant, when looked at as a side view, thus has a surface layer on top of it, with an outer surface (a first surface) and an inner surface (a second surface). On the inner surface is attached the porous part (its outer surface (first surface) facing the inner surface of the surface layer), i.e. underneath the surface layer. The implant does not comprise any other parts than these three, i.e. surface layer and porous part and the membrane layer made of collagen.

The implant may be used for reconstitution of bones following a trauma, a defect or a surgery of diseases. Implant reconstruction of damaged or missing parts of skeleton is performed by providing immediate repair of an anatomical shape and adequate mechanical support of the remaining pieces of bone with simultaneous penetration of blood and bone forming cells from the adjacent tissues to the implant. Typically the needs are in repairs of calvarial bone defects after neurosurgical operations and traumas, in reconstructions of bony orbital floors and jaw bones, but the implant can be used also in orthopaedics and spine surgery as well as in fixation of fragmented pieces of bone. In the presence of long bones weakened by diseases, or when parts of the cortical bone are lost, the implant can be used to reinforce the long bones and cover openings where cortical bone is lost.

The implant is preferably manufactured as follows. Firstly a mould for the surface layer is manufactured, based either on a standard form or a custom form. In the latter case, the custom form is typically obtained by medical imaging. The surface layer is then formed on the mould, for example by adding a few layers of fibre fabric or mat, together with the resin which forms the matrix. This step is well known in lamination techniques. Thereafter, the separately manufactured porous part is positioned on the surface layer and the surface layer is cured. During curing, the porous part becomes attached to the layer.

The surface layer may comprise one, two, three, four or five layers of fabric material, in the form of a fibre mat or a woven fibre fabric. There may of course also be more than five layers when a thicker surface layer is aimed for.

The description further relates to a use of an implant according to the present invention in dental and medical applications. Said use is for example for replacement of bones or support of the bone fractures. The specific embodiments and details listed above in connection with the composite also apply for this use.

Some embodiments of the invention are explained in more detail in the enclosed drawing, which is not to be construed as limiting the claims. The reference signs are also not to be construed as limiting the claims.

EXPERIMENTAL PART

Example 1

Manufacturing of an Implant with Porous Part Made of Bioactive Glass

A defected site of the patient's cranium was imaged with computer tomography (CT) and CT data was used to make a virtual 3D reconstruction, which was used to design the shape of the two parts of the implant: the surface layer, which is an anatomic form made of a fibre reinforced composite, and the porous part which forms an inner surface of bioactive glass. To fabricate the surface layer, a mould of the outer surface of the implant was made and two layers of E-glass fibre weave of 220 g/m$^2$ in weight was laminated to the mould after the weaves were been impregnated with resin systems of bisphenol-A-glycidyl dimethacrylate-triethylene glycol dimethacrylate system (50:50) comprising a heat sensitive initiator system of bezoylperoxide. The porous part made of bioactive glass was manufactured at the same time to be adhered to the fibre reinforced composite laminate, as follows.

Bioactive glass particles of 500 micrometers in size of glass type S53P4 were sintered in a platinum mould at temperature of 600° C. to the form of the open hole in the cranium. After sintering, the bioactive glass particles had formed the porous part of the implant. After sintering at the temperature mentioned above, there was interconnective porosity with pore size of 100 to 200 micrometers. Thickness of the bioactive glass part was the thickness of the cranial bone at the particular part of the cranium, in this case, six millimeters.

The porous part of the implant was placed on the resin impregnated glass fibre weaves on the mould. An excess of resin penetrated to the surface of the bioactive glass particle to the depth of less than one millimetres, and thus, more than five millimetres of the bioactive glass part remained without resin penetration. The resin was cured in vacuum at the temperature of 110° C. for 20 minutes, after which the implant was released from the mould and finished. The implant is sterilized and packed.

Example 2

Manufacturing of an Implant with a Porous Part Made of Hydroxyapatite

The manufacturing process of an implant with porous hydroxyapatite (HA) part followed the process described in Example 1, with the exception of the manufacturing of the part made of hydroxyapatite (the porous part). A block made of hydroxyapatite (Berkeley Advanced Biomaterials, Inc, USA) having interconnective porosity of 100 to 200 micrometers was milled to the form and thickness of the open hole in cranium. After milling the HA block, it was adhered to the fibre reinforced composite layer as described in Example 1.

DETAILED DESCRIPTION OF THE DRAWING

In the following, the same reference signs are used of the same or similar components in different embodiments and/or Figures.

FIG. 1 schematically shows an implant according to a first embodiment. The implant is arranged in an opening in the skull 1 of a patient. The implant consists of a surface layer 4 and a porous part 5 attached to its underside. The porous part 5 essentially fills the hole in the skull. The implant is arranged on the lamina dura 3 and brain 2 of the patient. The surface layer 4 overlaps with the skull 1 and hence extends over each edge of the porous part 5.

Figure 2:
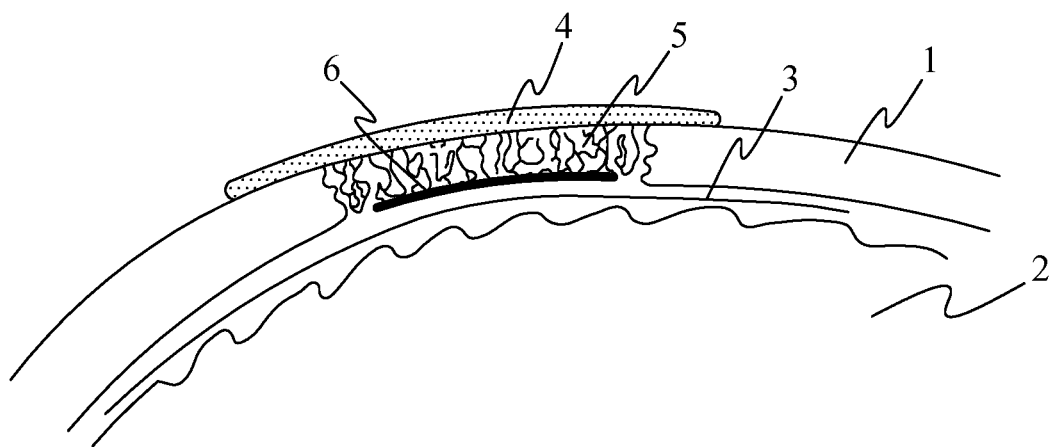
FIG. 2 schematically shows an implant according to a second embodiment.

FIG. 2 schematically shows an implant according to a second embodiment. In this embodiment, the second, inner surface of the porous part 5 is further mostly covered by a membrane 6 made of collagen. This membrane 6 prevents penetration of the dura mater to the porosities of the porous part 5 of the implant and may be beneficial in clinical cases where intracranial pressure is increased for a long period of time.

Figure 3:
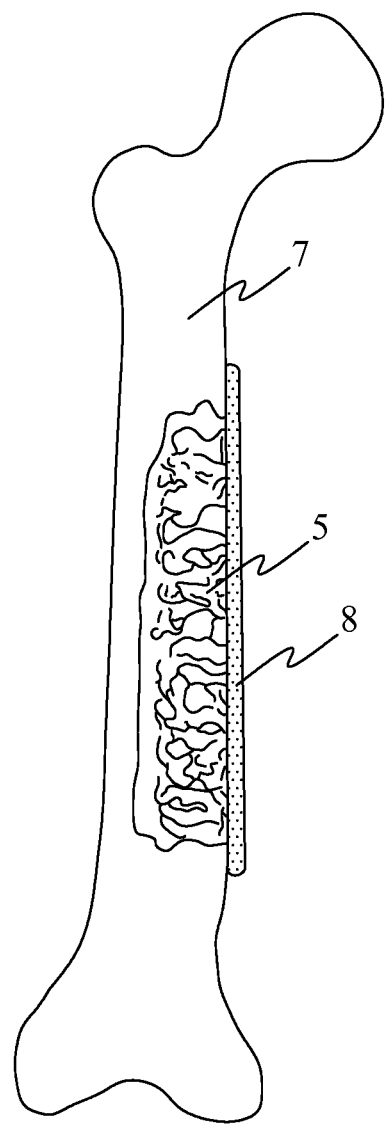
FIG. 3 schematically shows an implant according to a third embodiment.

FIG. 3 schematically shows an implant according to a third embodiment. In this embodiment, the implant is used for replacing a missing part of the femur bone after a bone tumour surgery. The porous part 5 of the implant fills the bone cavity and a fibre reinforced surface layer 8 made of slowly biodegradable materials reinforces the implant and gives it an anatomical outer shape.

Figure 4A:
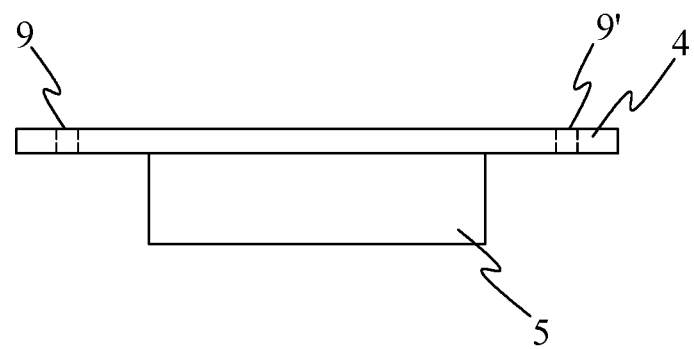
FIGS. 4A and 4B schematically illustrate an implant according to a fourth embodiment.
Figure 4B:
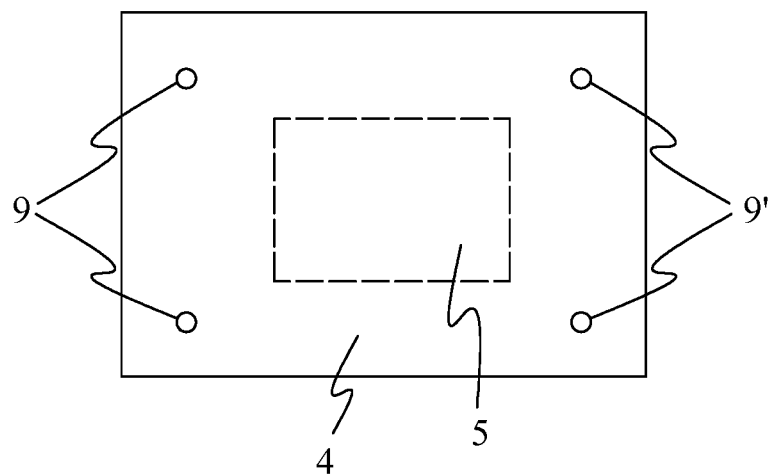

FIGS. 4A and 4B schematically illustrate a further embodiment. FIG. 4A is a side view showing the surface layer 4, wherein the first surface of the surface layer is the surface shown as an upper surface in the Figure and the second surface is the surface opposite to the first surface, namely the lower surface in the Figure. The porous part 5 is attached to the second surface of the porous part 4 and its first surface is also the surface that is shown as an upper surface in the Figure and the second surface is the lower surface in the Figure. Should a membrane made of collagen be used, it would be attached to the lower surface of the porous part but it would not cover the lower surface of the porous part entirely.

FIG. 4A further shows, in dashed line, openings 9 and 9' for attaching the implant to the bone of the patient. FIG. 4B shows the implant of FIG. 4A as a top view. The porous part 5 is shown in dashed lines underneath the surface layer 4 and each corner of the surface layer 4 is equipped with an opening 9, 9'. These openings can used for attaching the implant to the bone by screws.

The invention claimed is:

1. An implant consisting of
    a surface layer consisting of fibres and a matrix, having a first surface and a second surface opposite each other, and having a thickness that is at most 5% of the largest dimension of said surface layer,
    a porous biodegradable part having a first surface and a second surface opposite each other, wherein its first surface is attached to the second surface of the surface layer, and having a thickness of 1-8 mm, and
    a membrane layer made of collagen having a first surface and a second surface opposite each other, wherein its first surface is attached to the second surface of the porous part without covering the edges of the porous part,
    wherein the porous part comprises material selected from the group consisting of bioactive glass, bioactive ceramic, hydroxyapatite, tricalciumphosphate and mixtures thereof.

2. The implant according to claim 1, wherein the surface layer is non-biodegradable.

3. The implant according to claim 1, wherein the matrix is made of a resin selected from the group consisting of polyesters, epoxies, acrylates and mixtures thereof.

4. The implant according to claim 1, wherein the matrix resin is selected from the group consisting of substituted and unsubstituted dimethacrylates and methacrylates.

5. The implant according to claim 1, wherein the fibres of the surface layer are selected from the group consisting of S-glass fibres, E-glass fibres, carbon fibres, aramid fibres and mixtures thereof.

6. The implant according to claim 1, wherein the surface layer is biodegradable and its degradation rate is at least ten times longer than the degradation rate of the porous part.

7. The implant according to claim 6, wherein the matrix is made of a polymer selected from the group consisting of polylactide, polycaprolactone polymer, polysaccharide and mixtures thereof.

8. The implant according to claim 6, wherein the fibres of the surface layer are selected from the group consisting of bioactive glass fibres, calcium-sodium-metaphosphate fibres, cellulose fibres, hemp fibres, starch fibres and mixtures thereof.

9. The implant according to claim 1, wherein the porous part is in the form of a rectangle.

10. The implant according to claim 1, wherein the diameter of the fibres is 4-25 µm.

11. The implant according to claim 1, wherein thickness of the implant is 1.25-8.25 mm.

12. The implant according to claim 1, wherein thickness of the membrane is 0.05-0.80 mm.

13. The implant according to claim 1, wherein thickness of the surface layer is 0.2-4 mm.

* * * * *